United States Patent [19]

Frost et al.

[11] Patent Number: 4,883,549
[45] Date of Patent: Nov. 28, 1989

[54] METHOD OF ATTACHING A COMPOSITE ELASTIC MATERIAL TO AN ARTICLE

[75] Inventors: Johnathan E. Frost, Paris, Tex.; Eric T. Hsu; David M. Jackson, both of Roswell, Ga.; Thomas G. Olsen, Neenah; Robert L. Popp, Hortonville, both of Wis.

[73] Assignee: Kimberly-Clark Corporation, Neenah, Wis.

[21] Appl. No.: 280,465

[22] Filed: Dec. 6, 1988

[51] Int. Cl.[4] .............................................. B32B 31/16
[52] U.S. Cl. .................... 156/161; 2/243 R; 156/80; 156/164; 156/229; 264/288.8
[58] Field of Search ............... 156/160, 161, 163, 164, 156/229, 495, 494, 498, 80, 85, 176, 178; 2/243 R, 270, 401; 264/288.4, 288.8, 280, 230

[56] References Cited

U.S. PATENT DOCUMENTS

| | | | |
|---|---|---|---|
| 3,245,407 | 4/1966 | Mason | 128/284 |
| 3,639,917 | 2/1972 | Althouse | 2/270 |
| 3,644,157 | 2/1972 | Draper | 156/160 |
| 3,694,815 | 10/1972 | Burger | 2/224 A |
| 3,912,565 | 10/1975 | Koch et al. | 156/85 |
| 4,300,967 | 11/1981 | Sigl | 156/164 |
| 4,413,623 | 11/1983 | Pieniak | 604/365 |
| 4,443,511 | 4/1984 | Worden et al. | 264/288.8 X |
| 4,446,189 | 5/1984 | Romanek | 2/270 X |
| 4,450,026 | 5/1984 | Pieniak et al. | 156/164 |
| 4,507,163 | 3/1985 | Menard | 156/164 |
| 4,525,407 | 6/1985 | Ness | 428/138 |
| 4,543,154 | 9/1985 | Reiter | 156/73.1 |
| 4,552,795 | 11/1985 | Hansen et al. | 428/110 |
| 4,606,964 | 8/1986 | Wideman | 428/152 |
| 4,663,106 | 5/1987 | Pomplun et al. | 264/230 |
| 4,692,368 | 9/1987 | Taylor et al. | 156/164 X |
| 4,698,242 | 10/1987 | Salerno | 427/208.2 |
| 4,720,415 | 1/1988 | Vander Wielen et al. | 156/163 X |
| 4,781,966 | 11/1988 | Taylor | 604/370 X |

FOREIGN PATENT DOCUMENTS 2169930 7/1986 United Kingdom .

Primary Examiner—Michael W. Ball
Assistant Examiner—David W. Herb
Attorney, Agent, or Firm—Karl V. Sidor

[57] ABSTRACT

A method for attaching a composite elastic material to a gatherable article including the steps of stretching a composite elastic material; compressing said stretched composite elastic material to temporarily inhibit recovery of the composite elastic material; and attaching said temporarily inhibited composite elastic material to a gatherable article at least at two locations. Additionally, the temperature of the temporarily inhibited composite elastic material may be increased to facilitate recovery of the composite elastic material to within about 80 percent of its pre-stretched dimensions.

20 Claims, 2 Drawing Sheets

METHOD OF ATTACHING A COMPOSITE ELASTIC MATERIAL TO AN ARTICLE

FIELD OF THE INVENTION

The present invention relates to a method for attaching a composite elastic material to an article. Generally speaking, the present invention relates to a method for attaching a stretched composite elastic material to a gatherable article.

BACKGROUND OF THE INVENTION

Elastic materials have been attached to articles or garments such as, for example, disposable diapers at locations such as the waist and/or leg openings. The elastic materials are often stretched, attached to a gatherable article while in the stretched state and allowed to recover to their normal, prestretched state causing the gatherable article to pucker or shirr. Articles or garments elasticized in this manner may be expanded by the body of a wearer or the surface of an item to be covered. The resistance of the article to expansion will cause a snug fit between the article and the body or item to be covered at the location where the article contacts the body or item to be covered. Snug fitting locations may be desirable in products such as, for example, disposable diapers, medical garments, work-wear garments and feminine care products.

Applying stretched, actively elastic materials to a conformable or gatherable article is difficult because the elastic materials must be maintained in a stretched condition during at least part of the application process. Methods of temporarily inactivating stretched elastic material by freezing the elastic material have been developed. The frozen elastic material is attached to a gatherable substrate and then reactivated by heat so that it returns to its normal, pre-stretched condition. Additionally, heat shrinkable elastic materials have been developed which may be applied to a conformable substrate and heated to cause the elastic material to heat-shrink producing puckers and shirrs in the laminate.

DEFINITIONS

The term "elastic" is used herein to mean any material which, upon application of a biasing force, is stretchable, that is, elongatable, to a stretched, biased length which is at least about 125 percent, that is about one and one quarter, of its relaxed unbiased length, and which, will recover at least 40 percent of its elongation upon release of the stretching, elongating force. A hypothetical example would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, for example, 100 percent or more, and many of these will recover to substantially their original relaxed length, for example, to within 105 percent of their original relaxed length, upon release of the stretching force.

As used herein, the term "nonelastic" refers to any material which does not fall within the definition of "elastic," above.

As used herein, the term "recover" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation.

The term "composite elastic material" as used herein refers to a multilayer material having at least one elastic layer joined to at least one gatherable layer at least at two locations wherein the gatherable layer is gathered between the locations where it is joined to the elastic layer. A composite elastic material may be stretched to the extent that the nonelastic material gathered between the bond locations allows the elastic material to elongate. This type of composite elastic material is disclosed, for example, by Vander Wielen et al., U.S. Pat. No. 4,720,415 issued Jan. 19, 1988, which is hereby incorporated by reference.

The term "percent elongation" as used herein refers to a ratio determined by measuring the difference between the extended dimension and unextended dimension of a composite elastic material and dividing that difference by the unextended dimension of the composite elastic material.

The term "percent extension" as used herein refers to a ratio determined by measuring the difference between the stretch-to-stop or maximum extension and the unextended dimension of a composite elastic material and dividing that difference by the unextended dimension of the composite elastic material.

The term "total recovery" as used herein refers to the recovery of a stretched composite elastic material to generally within about 20 percent of its relaxed, pre-stretched dimensions.

The term "temporarily inhibit" as used herein refers to a delay in the total recovery of a stretched composite elastic material. The delay may be imparted by compressing the stretched composite elastic material so that the elastic and gatherable layers are temporarily joined. Partial recovery of a temporarily inhibited composite elastic material may occur immediately after the stretching force is removed from the composite elastic material but total recovery of such a temporarily inhibited composite elastic material will require more time than the total recovery of the same material which has not been temporarily inhibited. For example, total recovery of a stretched composite elastic material which has not been temporarily inhibited may be instantaneous but total recovery of a temporarily inhibited composite elastic material may take, for example, from about 5 to about 60 seconds.

As used herein, the term "nonwoven web" means a web having a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

As used herein, the term "microfibers" means small diameter fibers having an average diameter not greater than about 100 microns, for example, having a diameter of from about 0.5 microns to about 50 microns, or more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in Butin U.S. Pat. No. 3,849,241, the disclosure of which is hereby incorporated by reference.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spun-bonding mechanisms. The production of spun-bonded nonwoven webs is illustrated in patents such as, for example, in Appel et al. U.S. Pat. No. 4,340,563 and Dorschner et al. U.S. Pat. No. 3,692,618. The disclosures of these patents are hereby incorporated by reference.

As used herein, the term "sheet" means a layer which may either be a film or a nonwoven web.

As used herein, the term "palindromic laminate" means a multilayer laminate, for example, a composite elastic material which is substantially symmetrical. Exemplary palindromic laminates would have layer configurations of A/B/A, A/B/B/A, A/A/B/B/A/A, etc. Exemplary non-palindromic laminates would have layer configurations of A/B/C, A/B/C/A, A/C/B/D, etc.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solid solvents, particulates and materials added to enhance processability of the composition.

SUMMARY OF THE INVENTION

The present invention provides a method for attaching a composite elastic material to a gatherable article including the steps of:
stretching a composite elastic material;
compressing the stretched composite elastic material to temporarily inhibit total recovery of the composite elastic material; and
attaching the temporarily inhibited composite elastic material to the gatherable article at least at two locations.

The method may further include the step of increasing the temperature of the temporarily inhibited composite elastic material to facilitate recovery of the stretched composite elastic material to about 80 percent of its pre-stretched dimensions.

The composite elastic material includes at least one gatherable layer joined to at least one elastic sheet at least at two locations, with the gatherable layer being gathered between the two locations. The gatherable layer may be a film or a web such as, for example, a bonded carded web, a spunbonded web, a meltblown web. The gatherable layer may be made of polymers such as, for example, polyolefins, polyesters and polyamides. For example, the polyolefins may be one or more of polyethylene, polypropylene, polybutene, ethylene copolymers, propylene copolymers and butene copolymers. Alternatively, the gatherable layer may be a layer of crepe wadding, tissue or other pulp-based material. The present invention also provides that the basis weight of the gatherable layer should be at least about 5 grams per square meter (gsm), for example, from about 5 gsm to about 100 gsm.

The elastic sheet may be a pressure sensitive elastomer adhesive sheet. If the sheet is a nonwoven web of elastic fibers or pressure sensitive elastomer adhesive fibers, the fibers may be meltblown fibers. The meltblown fibers may include meltblown microfibers. The elastic sheet should be adapted to attach to the gatherable layer with a cohesive force of from about 3 to about 11 kilograms.

In one aspect of the present invention, the composite elastic material is stretched so that the gatherable layer is partially or fully extended between the locations where it is joined to the elastic sheet before the composite elastic material is compressed.

According to the present invention, the composite elastic material is temporarily inactivated by nipping the stretched material at a pressure of from about 300 to about 1500 pounds per linear inch (pli). Greater pressures may be used if they do not degrade the composite elastic material.

In another aspect of the present invention, a post-nip chill roll may be used to enhance the temporary inactivation achieved by nipping the material. The chill roll may be chilled to a temperature in the range from about 60° F. to about 33° F.

DETAILED DESCRIPTION OF THE INVENTION

Figure 1:
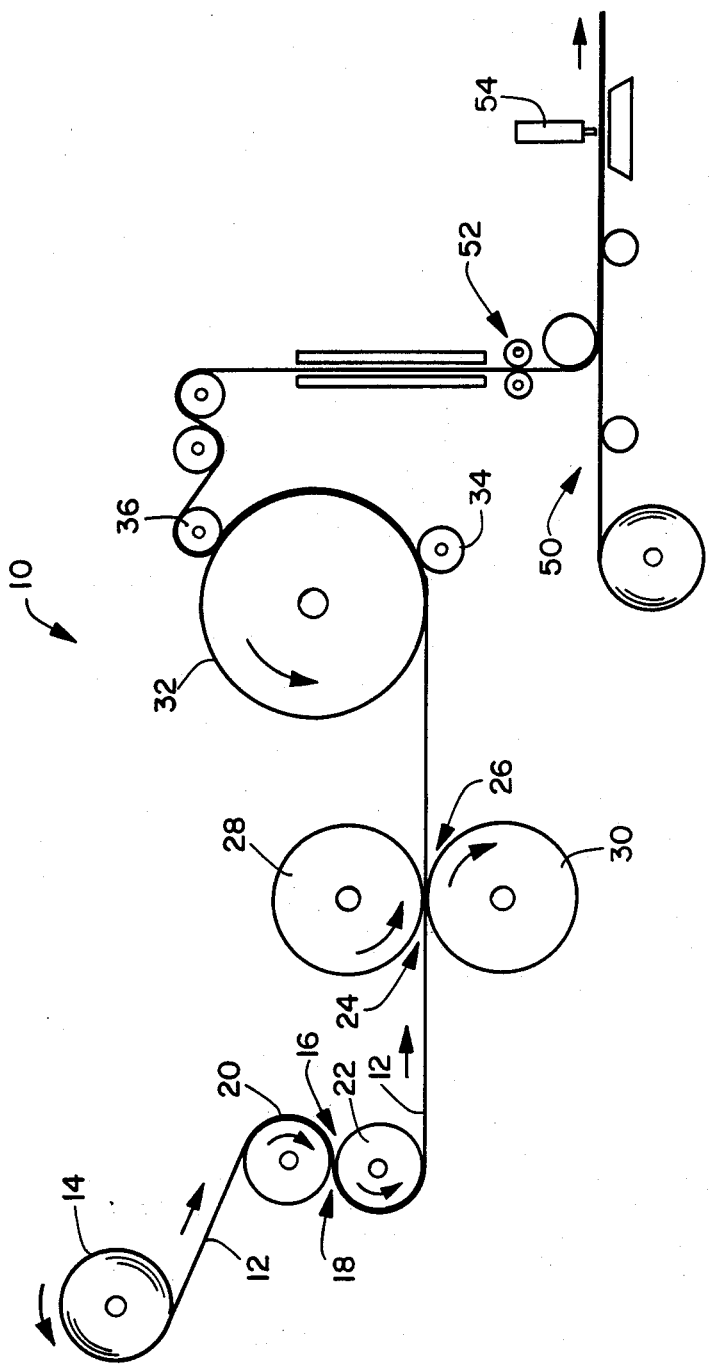
FIG. 1 is a schematic representation of an exemplary method for attaching a composite elastic material to a gatherable article.

Referring to the drawings where like reference numerals represent like materials or process steps and, in part, to FIG. 1, there is schematically illustrated at 10 a method for applying a composite elastic material 12 to a gatherable article.

A composite elastic material 12 is unwound from supply roll 14 of the composite elastic material. The composite elastic material 12 then travels in the direction indicated by the arrow associated therewith as a supply roll 14 rotates in the direction of the arrow associated therewith.

The composite elastic material 12 then passes through a nip 16 of an S-roll arrangement 18 formed by the stack rollers 20 and 22. Alternatively, individual components of the composite elastic material 12 may be formed by processes, such as, for example, spunbonding, meltblowing, film extrusion or bonded carded web processes, joined to form the elastic composite material 12 and then and passed directly through the nip 16 without first being stored on a supply roll.

The composite elastic material 12 passes through the nip 16 of the S-roll arrangement 18 in a reverse-S wrap path as indicated by the rotation direction arrows associated with the stack rollers 20 and 22. From the S-roll arrangement 18, the composite elastic material 12 passes through the nip 24 of a pressure nip roller arrangement 26 formed by the nip rollers 28 and 30. Because the peripheral linear speed of the stack rollers 20 and 22 of the S-roll arrangement 18 is controlled to be lower than the peripheral linear speed of the nip rollers 28 and 30 of the pressure nip roller arrangement 26, the composite elastic material 12 is tensioned between the S-roll arrangement 18 and the compression nip roller arrangement 26. By adjusting the difference in the speeds of the rollers, the composite elastic material 12 is tensioned so that it stretches a desired amount and is maintained in such stretched condition as it passes through the nip 24 of the compression nip roller arrangement 26. The nip rollers 28 and 30 are configured to compress the stretched composite elastic material 12 to temporarily inhibit total recovery.

A chill roll 32 may be used to enhance the temporary inactivation achieved by compressing the composite elastic material 12. Idler rolls 34 and 36 are used to maintain contact between the temporarily inactivated composite elastic material 12 and the chill roll 32. The temporarily inactivated material 12 is chilled while it contacts the surface of chill roll 32 causing an increase the period of inactivation. Temporary inactivation may be prolonged, for example, from about 2 to about 5 seconds by contact with the chill roll 32 for a period of about $\frac{1}{4}$ to about $1\frac{1}{2}$ seconds. Greater contact times will result in longer periods of inactivation. Chill roll 32 is maintained at a temperature lower than temperature of the temporarily inactivated material. Lower temperatures will also result in longer periods of inactivation. For example, temperatures from about 60° F. to about 33° F. have been found practical although lower temperatures may be used.

The temporarily inhibited composite elastic material 12 may then be attached to a gatherable article 50 utilizing, for example, adhesives from an adhesive applicator 52 or stitching from a stitchbonding apparatus 54.

Conventional drive means and other conventional devices which may be utilized in conjunction with the apparatus of FIG. 1 are well known and, for purposes of clarity, have not been illustrated in the schematic view of FIG. 1.

Figure 2:
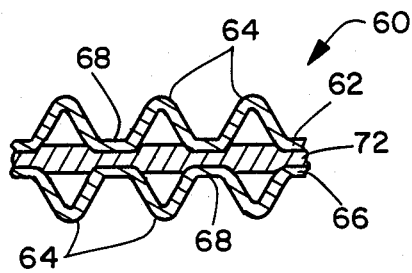
FIG. 2 is a cross-sectional view of an exemplary composite elastic laminate in the stretched condition.
Figure 3:
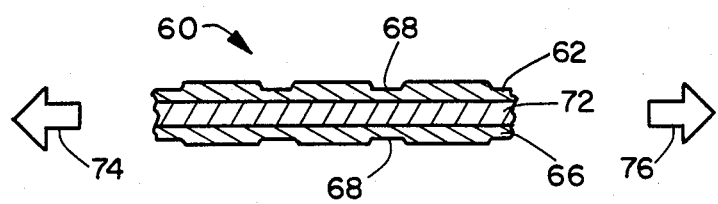
FIG. 3 is a cross-sectional view of the exemplary composite elastic laminate of FIG. 2 in the relaxed condition.

Referring now to FIG. 2, there is illustrated a cross-sectional view of a composite elastic material 60 in the stretched configuration to depict the structure of the multilayer material. The composite elastic material includes gatherable layers 62 and 66 joined to each side of an elastic sheet 72. Gatherable layers 62 and 66 are joined to the elastic sheet 72 at bond points 68. The gathers are not shown in FIG. 2 because the laminate is shown in a stretched condition due to application of tensioning force in the directions of the arrows 74 and 76. FIG. 3 is a cross-sectional view of the composite elastic material 60 shown in FIG. 2. Gathers 64 are present in FIG. 3 because the laminate 60 is depicted in a relaxed or unstretched condition. The gathers 64 result from the gathering of gatherable layers 62 and 66 between bond points 68 where the gatherable layers 62 and 66 are joined to the elastic sheet 72. Such a composite elastic material is commonly referred to as a "stretch-bonded laminate".

The composite elastic material 60 may include one or more layers of gatherable material joined to one or more layers of an elastic sheet. The multiple layers may be arranged to form a palindromic laminate. The basis weight of the composite elastic material in its relaxed, pre-stretched condition may range from about 50 gsm to about 250 gsm. A basis weight of about 165 gsm has been found to be particularly useful.

The elastic sheet 72 itself may be a multilayer material in that it may include two or more individual coherent webs or films. Additionally, the elastic sheet 72 may be a multilayer material in which one or more of the layers contain a mixture of elastic and nonelastic fibers and/or particulates. An example of the latter type of elastic web, reference is made to U.S. Pat. No. 4,209,563, incorporated herein by reference, in which elastomeric and non-elastomeric fibers are commingled to form a single coherent web of randomly dispersed fibers. Another example of such a composite web would be one made by a technique such as disclosed in Richard A. Anderson et al. U.S. Pat. No. 4,100,324, issued July 11, 1978 and also incorporated herein by reference. That patent discloses a nonwoven material which includes a mixture of meltblown thermoplastic fibers and other materials which are combined in the gas stream in which the meltblown fibers are borne so that an intimate entangled commingling of meltblown thermoplastic fibers and other materials, e.g., wood pulp, staple fibers or particulates such as, for example, hydrocolloid (hydrogel) particulates commonly referred to as superabsorbents occurs prior to collection of the fibers upon a collecting device to form a coherent web of randomly dispersed fibers.

The elastic sheet 72 may be made from any material which may be manufactured in sheet form. Generally, any suitable elastomeric fiber forming resins or blends containing the same may be utilized for the nonwoven webs of elastomeric fibers of the invention and any suitable elastomeric film forming resins or blends containing the same may be utilized for the elastomeric films of the invention.

For example, the elastic sheet 72 may be made from elastomeric block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated $(A-B)_m-X$, wherein X is a polyfunctional atom or molecule and in which each $(A-B)_m-$ radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded (e.g., by meltblowing), and without limitation as to the number of blocks. The elastic sheet 72 may be formed from, for example, elastomeric (polystyrene/-poly(ethylene-butylene)polystyrene) block copolymers available from the Shell Chemical Company under the trademark KRATON G. One such block copolymer may be, for example, KRATON G-1657.

Other exemplary elastomeric materials which may be used as the elastomeric polymer in the blend include polyurethane elastomeric materials such as, for example, those available under the trademark ESTANE from B. F. Goodrich & Co., polyamide elastomeric materials such as, for example, those available under the trademark PEBAX from the Rilsan Company and polyester elastomeric materials such as, for example, those available under the trade designation Hytrel from E. I. DuPont De Nemours & Company. Formation of elastic sheets from polyester elastic materials is disclosed in, for example, Morman et al. U.S. Pat. No. 4,741,949, hereby incorporated by reference.

A polyolefin may also be blended with the elastomeric polymer to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. Two or more of the polyolefins may be utilized. Extrudable blends of elastomeric polymers and polyolefins are disclosed in, for example, Wisneski et al. U.S. Pat. No. 4,663,220, hereby incorporated by reference.

A particularly useful polyethylene may be obtained from U.S.I. Chemical Company under the trade designation Petrothene NA601 (also referred to herein as PE NA601). Information obtained from U.S.I Chemical Company states that PE NA601 is a low molecular weight, low density polyethylene for application in the areas of hot melt adhesives and coatings. U.S.I. has also stated that PE NA601 has the following nominal values: (1) a Brookfield viscosity, cP at 150° C. of 8,500 and at 190° C. of 3,300 when measured in accordance with ASTM D 3236; (2) a density of 0.903 grams per cubic centimeter when measured in accordance with ASTM D 1505; (3) and equivalent Melt index of 2,000 grams per 10 minutes when measured in accordance with ASTM D 1238; (4) a ring and ball softening point of 102° C. when measured in accordance with ASTM E 28; (5) a tensile strength of 850 pounds per square inch when measured in accordance with ASTM D 638; (6) an elongation of 90% when measured in accordance with ASTM D638; (7) a modulus of rigidity, $T_F$(45,000) of $-34°$ C; and (8) a penetration hardness (tenths of mm) at 77° F. (Fahrenheit) of 3.6. Another useful polyethylene is identified by the trade designation EPOLENE C-10 and may be obtained from the Eastman Chemical Company. Specific information about the material may be obtained from the manufacturer.

The elastic sheet 72 is a pressure sensitive elastomer adhesive sheet. For example, the elastic material itself may be tacky or, alternatively, a compatible tackifying resin may be added to the extrudable elastomeric compositions described above or an adhesive may be applied to the elastic sheet to provide an elastic sheet that can act as a pressure sensitive adhesive. Although the inventors should not be held to a particular theory of operation, it is believed that the tackiness of the elastic sheet 72 causes temporary bonding of the stretched elastic sheet 72 to the gatherable layers 62 and 66 after compression so that the elastic sheet 72 is temporarily inhibited from recovering to its pre-stretched dimensions.

In regard to the tackifying resins and tackified extrudable elastomeric compositions, note the resins and compositions as described in U.S. patent application Ser. No. 919,901, now J. S. Keiffer and T. J. Wisneski U.S. Pat. No. 4,789,699, filed Oct. 15, 1986 for "Ambient Temperature Bondable Elastomeric Nonwoven Web", hereby incorporated by reference. Any tackifier resin can be used which is compatible with the elastomeric polymer and can withstand the high processing (e.g., extrusion) temperatures. If blending materials such as, for example, polyolefins or extending oils are used, the tackifier resin should also be compatible with those blending materials. Generally, hydrogenated hydrocarbon resins are useful tackifying resins because of their better temperature stability. REGALREZ TM 1126 and ARKON TM P series tackifiers are examples of hydrogenated hydrocarbon resins. ZONATAK TM 501 lite is an example of a terpene hydrocarbon. Of course, the present invention is not limited to use of such three tackifying resins, and other tackifying resins which are compatible with the composition and can withstand the high processing temperatures, can also be used.

REGALREZ hydrocarbon resins are available from Hercules Incorporated. Grades 1094, 3102, 6108 and 1126 are highly stable, light-colored, low molecular weight, nonpolar resins suggested for use in plastics modification, adhesives, coatings, sealants and caulks. The resins are compatible with a wide variety of oils, waxes, alkyds, plastics and elastomers and are soluble in common organic solvents. Product specifications of the above-mentioned grades of REGALREZ resin and compatibility information are set forth in Tables 1 and 2.

ARKON P series resins are available from Arakawa Chemical (U.S.A.), Inc., and are synthetic tackifying resins for pressure sensitive adhesives which are based on hydrocarbon resins. The general properties of ARKON P series resins are set forth in Table 3.

The components of the blends utilized in the present invention may be present over broad ranges of the amounts of each component, such amounts being easily determined by one of ordinary skill in the art. As a guide, when utilizing an A-B-A block copolymer, a polyolefin, and a resin tackifier as the three components of the extrudable composition, the following broad and preferred ranges, as shown in Table 4, are exemplary. It is emphasized that these ranges are merely illustrative, serving as a guide for amounts of the various components in the composition.

As stated previously, while the present invention has been discussed in terms of a three-component extrudable composition of (1) elastomeric polymer; (2) polyolefin; and (3) resin tackifier, the polyolefin, which functions as a viscosity-reducer for the total composition, can be substituted by other compatible viscosity reducers, or can be eliminated altogether where the tackifying resin can also act as the viscosity reducer. For example, low molecular weight hydrocarbon resin tackifiers such as, for example, REGALREZ 1126 can also act as the viscosity reducer, whereby the extrudable composition can be comprised of the elastomeric polymer and tackifying resin (e.g., REGALREZ 1126).

While the principle components of the elastic sheet 12 have been described as the foregoing, the elastic sheet is not limited to only those components and may include other components that do not adversely affect the desired properties of the elastic sheet. Exemplary materials which could be used as additional components would include, without limitation, pigments, antioxidants, stabilizers, surfactants, waxes, flow promoters, solid solvents, particulates and materials added to enhance processability of the composition.

The elastic sheet 72 may be a nonwoven web (e.g., a film, porous film, or fibrous nonwoven web) formed by extrusion techniques. For example, the elastic sheet 72 may be formed by meltblowing a blend including about 63% by weight KRATON G-1657 block copolymer, about 20% Polyethylene NA601 and about 17% REGALREZ 1126 tackifying resin having a melt flow of from about 12 grams per ten minutes to about 18 grams per ten minutes when measured at 190° C. and under a 2160 gram load; an elongation of about 750%; a modulus of elongation at 100% of from about 155 to about 200 psi; and a modulus of elongation at 300% of from about 200 to about 250 psi. More particularly, the blend may have a melt flow of about 15 grams per ten minutes when measured at 190° C. and under a 2160 gram load; an elongation of about 750%; a modulus of elongation at 100% of about 175 psi; and a modulus of elongation at 300% of about 225 psi. The blend may be meltblown at a temperature of from about 500 to about 600° F.

If the elastic sheet 72 is an elastic nonwoven web, the basis weight of the web may range from about 40 to about 200 gsm. Basis weights of about 85 to about 110 gsm are particularly useful. If the elastic sheet 72 is a film, the film may range in thickness from about 1 to about 4 mils.

Various gatherable materials can be utilized and are discussed, for example, in previously referenced U.S. Pat. No. 4,720,415.

The gatherable materials can include, but are not limited to non-elastic nonwoven webs such as, for example, bonded carded non-elastic polyester or non-elastic polypropylene fiber web, spunbonded non-elastic polyester or polypropylene non-elastic fiber web, non-elastic cellulosic fiber webs, e.g., cotton fiber webs, polyamide fiber webs, e.g., nylon 6-6 webs, and blends of two or more of the foregoing. Additionally, crepe wadding, tissue or other pulp-based materials may be used. The desirable basis weight of the gatherable webs depends upon various factors including the retraction force of the elastic sheet and the desired retraction by the elastic sheet. The gatherable material should have sufficient stiffness so that it can resist the retraction force of the elastic sheet when the stretched elastic sheet is temporarily bonded to the gatherable web. Exemplary, and not limiting, basis weight values for the gatherable web are from about 5 to about 100 grams per square meter (gsm), for example, from about 10 to about 30 gsm. Generally, elastic sheets having greater retraction forces will require gatherable webs having greater basis weights.

Composite elastic materials such as, for example, stretch-bonded laminates may have a maximum elongation or stretch-to-stop which is affected by the amount of inelastic gatherable material gathered between the locations where the gatherable material is joined to the elastic sheet. When the gatherable material is fully extended the composite elastic material can be described as reaching its maximum or 100 percent extension. When extended beyond its maximum extension, the inelastic gatherable material necks or constricts causing undesirable product attributes or breaks causing disruptions in the manufacturing process. When the extension of the composite elastic material is controlled to be equal or slightly lower than the maximum extension, necking and breaks are minimized. Additionally, material usage, product attributes and process efficiency are maximized.

Figure 4:
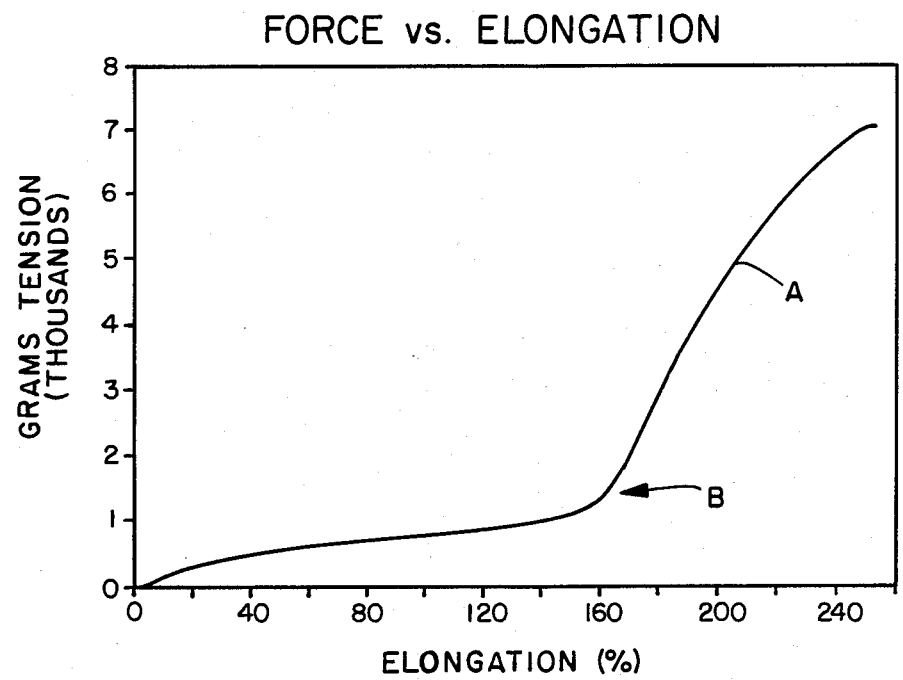
FIG. 4 is an exemplary force versus elongation curve for a typical stretch-bonded laminate material.

Illustrated at FIG. 4 is an exemplary force versus extension curve for a typical stretch-bonded laminate. The tensioning force required to extend the stretch-bonded laminate to its maximum elongation may be determined by plotting the tension versus elongation of a stretch-bonded laminate to identify curve A. The tension required for maximum extension may be found in the general range of tension force values corresponding to the region B where there is a substantial increase in the slope of curve A, i.e., the point of inflection.

With regard to the tension used to fully extend the composite elastic material, one skilled in the art will appreciate that the tension which is applied for maximum extension will depend not only on the type of elastomeric polymer, tackifying resin or other components of the elastic sheet but also on the basis weights of the elastic materials, the process used to make the material and the stretch characteristics of the material. However, for a given elastic material, and in view of the herein contained disclosure the processing conditions necessary to achieve satisfactory extension of the elastic sheets can be readily determined by one of skill in the art.

The stretched composite elastic material 12 may be nipped utilizing various combinations of nip rollers such as, for example, roller arrangements combining rubber/steel, nylon/steel or steel/steel rollers. Nip roller combinations such as rubber (Shore A 100)/steel nip rollers have been operated at a pressure of from about 350 to about 700 pounds per linear inch to inactivate a composite elastic material. In general, greater pressures will result in longer periods of inactivation. However, some rubber rollers tend to heat up when operated at high pressures and/or speeds. Steel rollers may be used at pressures of from about 500 to about 1500 pounds per linear inch to inactivate a composite elastic material. Particularly useful results have been achieved at pressures between about 950 and 1100 pounds per linear inch. Greater pressures may be used with the upper limit being pressures at which the elastic material begins to degrade.

With regard to the pressure used to temporarily inactivate the stretched elastic sheet, one skilled in the art will appreciate that the pressures at which the materials are subjected to for inactivation will depend not only on the type of elastomeric polymer, tackifying resin or other components of the elastic sheet but also on the degree of stretching of the elastic sheet, the basis weights of the materials, the residence time of the materials in the nip of the compression rolls and the specific materials used in the compression rolls. However, for a given combination of materials and in view of the herein contained disclosure the processing conditions necessary to achieve satisfactory temporary inactivation of the stretched elastic sheets can be readily determined by one of skill in the art.

The nip rollers utilized to compress the composite elastic material should be maintained at a temperature ranging from about 60° F. to about 100° F. In particular, useful results have been obtained when the nip rollers were maintained at ambient temperature, i.e., about 70° F. The use of a chilled post-nip roll has also been found to prolong temporary inactivation of the compressed composite elastic material.

The tackiness of the elastic sheet also affects the ability of the composite elastic material to be inactivated. When compressed, the elastic sheet should be adapted to adhere to the gatherable layer with a cohesive force of from about 3 kilograms to about 11 kilograms, for example, from about 7 to about 9 kilograms. The elastic sheet itself may be tacky or an adhesive may be applied to the elastic sheet or the gatherable material. If the elastic sheet itself is tacky, the tackiness may be from the inherent tackiness of the material used to form the sheet.

Alternatively, an adhesive or tackifier may be blended with the elastic material used to make the elastic sheet to provide or increase tackiness. Generally, larger amounts of tackifier added to the blend result in greater tackiness of the elastic sheet and correspondingly longer period of inactivation when the elastic sheet compressed. However, too much tackifier degrades the stretch properties of the elastic sheet.

The composite elastic material 60 may be attached to a gatherable article at least at two locations by means such as, for example, adhesives, hot-melt adhesives, stitchbonding, ultrasonic bonding, and pressure and/or thermal spot bonding. If composite elastic material 60 is a two-layer laminate having an elastic surface and a gatherable material surface, the elastic surface may be attached directly to the gatherable article at least at two locations. If the gatherable material surface of composite elastic material 60 is attached directly to the gatherable article, the gatherable material surface may be completely bonded to the gatherable article.

Once the stretched and inactivated composite elastic material is attached to the gatherable article, the composite elastic material may be reactivated by raising the temperature of the composite elastic material so that it recovers to its relaxed, pre-stretched state. The temporarily inhibited composite elastic material will recover almost instantaneously to its relaxed, prestretched dimensions once the temperature of the sheet is raised to detach the temporary bonds between the elastic sheet and the gatherable material of the composite elastic material. If not heated, the temporary bonds will slowly detach at room temperatures and the temporarily inactivated material will recover to its pre-stretched dimensions.

The temperature may be raised any suitable radiant, convective or conductive heating means such as, for example, forced hot air, infrared heat lamps, contact with a heated surface and/or a heated liquid. The temperature change required to reactivate the elastic sheet may vary according to factors such as, for example, the basis weight of the elastic sheet, the tackiness of the elastic sheet, the degree the material was stretched, the compression force applied to inactivate the stretched elastic sheet, and the intensity and method of heating.

Good recovery has been obtained by raising the temperature of the composite elastic material from about 120° F. to about 170° F. Typically, temporarily inactivated materials recover to their pre-stretch dimensions when briefly exposed to forced hot air maintained at a temperature in the range of about 150° F. to about 160° F.

EXAMPLE

Composite Elastic Material

A composite elastic material was made from a gatherable web of spunbonded polypropylene having a basis weight of about 14 gsm joined to both sides of an elastic web of meltblown fibers having a basis weight of about 100 gsm utilizing a patterned bonder roll arrangement. The elastic web was formed from a blend containing, by weight, about 63% KRATON G 1657 block copolymer, about 20% polyethylene PE NA601, and about 17% REGALREZ 1126 tackifying resin. The layers were joined so the gatherable spunbonded web gathered between the locations where joined the elastic layer. Such a composite elastic material is typically referred to as a stretch-bonded laminate. The overall basis weight of the stretch-bonded laminate was about 165 gsm while the material was in the relaxed, unstretched condition.

Cohesion of the Composite Elastic Material

The cohesiveness of the elastic web was determined by measuring the force required to pull apart a stretch bonded laminate in the Z coordinate. The sample measured approximately 2 inches wide by 4 inches long between and was placed between two pressure plates covered with double coated pressure sensitive tape. The force required to pull the stretch-bonded laminate apart was measured using an "Accuforce Cadet" 0–20 kg digital force gauge available from the Hunter Spring Company. The results for the stretch bonded laminate having an elastic Kraton web are given in Table 5 under the heading "Kraton".

Other stretch-bonded laminate materials were tested to measure the cohesiveness of elastic layers containing different components. An elastic layer identified in Table 5 by the heading "RP 6517" was formed from a blend containing about 63% by weight KRATON G 1657 block copolymer, about 20% Epolene C-10 polyethylene, and about 17% Arkon P-125 tackifying resin. Another elastic layer, identified in Table 5 by the heading "RP 6518" was formed from a blend containing about 63% by weight KRATON G 1657 block copolymer, about 20% polyethylene PE NA601, and about 17% Arkon P-125 tackifying resin.

Maximum Elongation of the Elastic Material

The composite elastic material was stretched and the force required to achieve different amounts of extension was measured using an Instron Model 1122 Universal Testing Instrument. The sample was 2 and ⅛ inches wide and the distance between the jaws of the tester was 4 inches. The jaw separation rate was approximately 20 inches per minute. The results are reported in Table 3. Maximum or 100 percent extension of the gatherable web was achieved at 160 percent elongation. A tensioning force of approximately 1500 rams was required to achieve 100 percent extension for the 2 and ⅛ inch wide strip.

Inactivation of the Elastic Material

Unextended samples were marked at points approximately 36 inches apart and stretched from about 48 to about 61 inches which was approximately 99 percent extension. The marked and stretched composite elastic materials were passed through the nip of a steel/steel pressure roller arrangement and compressed at pressures of about 180, 360, 400, and 550 pli. The retraction of the samples was measured utilizing a yard stick and a stopwatch. The results are given in Tables 7-10 wherein the extended length of the sample upon release of the stretching force is reported under the row heading "−3 seconds". The extended length of the sample when place along the measuring stick is reported under the row heading "0 seconds".

Disclosure of the presently preferred embodiment of the invention is intended to illustrate and not to limit the invention. It is understood that those of skill in the art should be capable of making numerous modifications without departing from the true spirit and scope of the invention.

TABLE 1

| | REGALREZ ® Resins | | | |
|---|---|---|---|---|
| | 1094 | 3102 | 6108 | 1126 |
| Softening point, R&B, °C. | 90–98 | 98–106 | 104–112 | 122–130 |
| Color | crystal-clear | | | |
| Typical Properties | | | | |
| Softening point, R&B, °C. | 94 | 102 | 108 | 126 |
| Color | crystal-clear | | | |
| Acid number | <1 | | | |
| Saponification number | <1 | | | |
| Specific gravity at 21° C. | 0.99 | 1.04 | 1.01 | 0.97 |
| Flashpoint, COC, °C. (°F.) | 235(455) | 293(560) | 243(470) | 243(470) |
| Melt viscosity, °C. | | | | |
| 1 poise | 190 | 196 | 200 | 209 |
| 10 poises | 151 | 164 | 168 | 182 |
| 100 poises | 126 | 149 | 143 | 159 |
| Glass transition (Tg), °C. | 33 | 51 | 52 | 65 |

TABLE 2

| Compatibility Information | | | | |
|---|---|---|---|---|
| | REGALREZ ® Resins | | | |
| Compatibility With | 1094 | 3102 | 6108 | 1126 |
| Natural rubber | G | G | G | G |
| SBR 1011 | P | G | G | P |
| KRATON 1107 (MB) | G | G | E | G |
| KRATON 1101 (MB) | P | F | G | P |
| Styrene end block copolymers | P | G | F | P |
| KRATON "G" (MB) | G | F | G | G |
| E/VA copolymers | | | | |
| (low vinyl acetate content) | E | F | G | E |
| (high vinyl acetate content) | P | E | F | P |
| Paraffin wax | E | G | E | E |
| Microcrystalline wax | E | G | E | E |

KEY: E = Excellent; G = Good; F = Fair; P = Poor

TABLE 3

| | ARKON P-70 | ARKON P-90 | ARKON P-100 | ARKON P-115 | ARKON P-125 |
|---|---|---|---|---|---|
| Color number (Hansen) | 50 | 50 | 50 | 50 | 50 |
| Softening point | 70° C. | 90° C. | 100° C. | 115° C. | 125° C. |
| Acid number | 0 | 0 | 0 | 0 | 0 |
| Specific gravity (20° C.) | — | 0.973 | 0.982 | 0.985 | 0.989 |
| Refractive index (20° C.) | — | 1.515 | 1.519 | 1.523 | 1.530 |
| Molecular Weight | — | 650 | 700 | 850 | 1000 |
| Ash (%) | — | 0.05 | 0.05 | 0.05 | 0.05 |
| Dielectric constant | | | | | |
| 50 MC | — | 2.3 | 2.3 | 2.3 | 2.3 |
| 1000 MC | — | 2.3 | 2.3 | 2.3 | 2.3 |
| Loss tangent | | | | | |
| 50 MC | — | 0.0001 max | 0.0001 max | 0.0001 max | 0.0001 max |
| 1000 MC | — | 0.0001 max | 0.0001 max | 0.0001 max | 0.0001 max |

TABLE 4

| POLYMER | WEIGHT PERCENT |
|---|---|
| A-B-A block Copolymer | 60–70% |
| Polyolefin | 15–25% |
| Resin Tackifier | 13–20% |

TABLE 5

| | COHESION (Kg) | |
|---|---|---|
| KRATON | RP 6517 | RP 6518 |
| 7.78 | 8.26 | 7.93 |
| 9.15 | 8.62 | 8.27 |
| 9.24 | 8.64 | 8.84 |
| 8.87 | 8.99 | 6.18 |
| | 9.09 | |
| AVERAGE 8.76 | 9.75 | AVERAGE 7.80 |
| | AVERAGE 8.89 | |

TABLE 6

| TENSION 2⅛ inch wide sample (GRAMS FORCE) | ELONGATION % |
|---|---|
| 250 | 20 |
| 500 | 40 |
| 700 | 60 |
| 900 | 80 |
| 1000 | 100 |
| 1100 | 120 |
| 1250 | 140 |
| 1500 | 160 |
| 3000 | 180 |
| 5000 | 200 |

TABLE 6-continued

| TENSION 2½ inch wide sample (GRAMS FORCE) | ELONGATION % |
|---|---|
| 6000 | 220 |

TABLE 7

| | Sample compressed at 180 pli | |
|---|---|---|
| TIME (SECONDS) | EXTENDED LENGTH (INCHES) | DISTANCE (INCHES) |
| −3 | 56.5 | 54.5 |
| 0 | 49.0 | 47.0 |
| 5 | 42.0 | 43.5 |
| 10 | 41.0 | 42.5 |
| 15 | 40.25 | 41.75 |
| 20 | 40.0 | 41.0 |
| 30 | 39.25 | 40.25 |
| 45 | 38.5 | 39.5 |
| 60 | 38.0 | 39.0 |
| 90 | 37.5 | 38.5 |
| 120 | 37.25 | 38.0 |
| 180 | 36.75 | 37.75 |
| 240 | 36.5 | 37.5 |

TABLE 8

| | Sample Compressed at 360 pli | | |
|---|---|---|---|
| TIME SECONDS | DISTANCE (INCHES) | DISTANCE (INCHES) | DISTANCE (INCHES) |
| −3 | 61.0 | 53.0 | 48.0 |
| 0 | 55.0 | 49.0 | 45.0 |
| 5 | 53.0 | 46.25 | 41.75 |
| 10 | 52.5 | 45.5 | 40.75 |
| 15 | 51.5 | 44.75 | 40.125 |
| 20 | 51.0 | 44.0 | 39.75 |
| 30 | 50.25 | 43.25 | 39.0 |
| 45 | 49.125 | 42.5 | 38.375 |
| 60 | 48.5 | 41.25 | 38.0 |
| 90 | 48.0 | 41.25 | 37.25 |
| 120 | 47.5 | 40.75 | 37.0 |
| 180 | 47.0 | 40.25 | 36.375 |
| 240 | 46.5 | 40.0 | 36.0 |

TABLE 9

| | Sample compressed at 460 pli | |
|---|---|---|
| TIME SECONDS | DISTANCE (INCHES) | DISTANCE (INCHES) |
| −3 | 54.0 | 53.0 |
| 0 | 51.0 | 49.0 |
| 5 | 47.75 | 46.0 |
| 10 | 46.75 | 44.75 |
| 15 | 46.0 | 44.0 |
| 20 | 45.5 | 43.625 |
| 30 | 44.75 | 43.0 |
| 45 | 44.0 | 42.25 |
| 60 | 43.5 | 41.75 |
| 90 | 42.875 | 41.125 |
| 120 | 42.375 | 40.75 |
| 180 | 41.75 | 40.125 |
| 240 | 41.25 | 39.75 |

TABLE 10

| | Sample compressed at 550 pli | |
|---|---|---|
| TIME (SECONDS) | DISTANCE (INCHES) | DISTANCE (INCHES) |
| −3 | 51.0 | 50.5 |
| 0 | 48.0 | 48.5 |
| 5 | 46.0 | 46.5 |
| 10 | 45.0 | 45.75 |
| 15 | 44.5 | 44.25 |
| 20 | 44.25 | 44.875 |
| 30 | 43.5 | 44.25 |
| 45 | 42.75 | 43.625 |
| 60 | 42.25 | 43.25 |
| 90 | 41.75 | 42.625 |
| 120 | 41.25 | 42.125 |
| 180 | 40.75 | 41.5 |
| 240 | 40.5 | 41.125 |

What is claimed is:

1. A method for attaching a composite elastic material to a gatherable article comprising the steps of:
   providing a composite elastic material including at least one elastic sheet joined to at least one gatherable layer at least at two locations, said gatherable layer being gathered between said locations;
   stretching said composite elastic material so that said gatherable layer is at least partially extended between the locations where the gatherable layer is joined to the elastic sheet;
   compressing said stretched composite elastic material to press at least a portion of said gatherable layer against at least a portion of said elastic sheet to temporarily inhibit total recovery of said composite elastic material;
   attaching said temporarily inhibited composite elastic material to said gatherable article at least at two locations,
   wherein said temporarily inhibited composite elastic material is adapted, upon recovery, to gather said gatherable article.

2. The method of claim 1, further comprising the step of increasing the temperature of said temporarily inhibited composite elastic material to facilitate recovery of said composite elastic material to within about 80 percent of its prestretched dimensions.

3. The method of claim 1, wherein said elastic sheet is an elastic web of meltblown fibers.

4. The method of claim 3, wherein said meltblown fibers include meltblown microfibers.

5. The method of claim 1, wherein said elastic sheet is a pressure sensitive elastomer adhesive sheet formed from a blend of an elastomeric polymer and a tackifying resin.

6. The method of claim 5, wherein said pressure sensitive elastomer adhesive sheet is a pressure sensitive elastomer adhesive web of meltblown fibers.

7. The method of claim 5, wherein said blend also includes a polyolefin to lower the viscosity of said blend so that said blend may be extruded to form fibers without degrading the elastomeric polymer.

8. The method of claim 6, wherein said meltblown fibers include meltblown microfibers.

9. The method of claim 1, wherein said composite elastic material is stretched so that said gatherable web is fully extended between the locations where the gatherable web is joined to the elastic sheet.

10. The method of claim 5, wherein elastomeric polymer is an elastomeric block copolymer.

11. The method of claim 10, wherein the elastomeric block copolymer is selected from the group consisting of A-B-A' block copolymers, A-B block copolymers and $(A-B)_m-X$ radial block copolymers, where A and A' are thermoplastic polymer blocks which can be the same or different and B is a rubbery polymer block, and where X is an inorganic or organic polyfunctional atom or molecule, with m being an integer having the same value as the functional group originally present in X.

12. The method of claim 5, wherein the tackifying resin is selected from the group consisting of hydrogenated hydrocarbon resins and terpene hydrocarbon resins.

13. The method of claim 7, wherein the polyolefin is selected from the group consisting of one or more of polyethylene, polypropylene, polybutene, ethylene copolymers, propylene copolymers, and butene copolymers.

14. The method of claim 7, wherein the blend comprises, by weight, from about 60 to about 70 percent A-B-A' block copolymer, from about 15 to about ≃percent polyolefin and from about 13 to about 20 percent tackifying resin.

15. The method of claim 1, wherein the gatherable layer is a web selected from the group consisting of one or more of a bonded carded web of fibers, a web of spunbonded fibers and a web of meltblown fibers.

16. The method of claim 15 wherein the fibers comprise a polymer selected from the group consisting of polyolefins, polyesters and polyamides.

17. The method of claim 16, wherein the polyolefin is selected from the group consisting of one or more of polyethylene, polypropylene, polybutene, ethylene copolymers, propylene copolymers and butene copolymers.

18. The method of claim 1 wherein said elastic sheet is adapted to temporarily adhere to the gatherable layer with a cohesive force of at least 3 kilograms.

19. A method for attaching a composite elastic material to a gatherable article comprising the steps of:
stretching a composite elastic material so that said gatherable layer is at least partially extended between the locations where the gatherable layer is joined to the elastic sheet;
compressing said stretched composite elastic material to press at least a portion of said gatherable layer against at least a portion of said pressure sensitive elastomer adhesive sheet to temporarily inhibit total recovery of said composite elastic material; and
attaching said temporarily inhibited composite elastic material to said gatherable article at least at two locations, wherein said temporarily inhibited composite elastic material is adapted, upon recovery, to gather said gatherable article and wherein said composite elastic material includes at least one pressure sensitive elastomer adhesive sheet joined to at least one gatherable layer at least at two locations, aid gatherable layer being gathered between said two locations.

20. The method of claim 1, wherein said stretched elastic composite material is chilled after being compressed.

* * * * *